United States Patent [19]

Leight

[11] Patent Number: 4,774,938

[45] Date of Patent: Oct. 4, 1988

[54] SLOW RECOVERY EARPLUG WITH LARGELY IMPENETRABLE SURFACE

[75] Inventor: Howard S. Leight, Malibu, Calif.

[73] Assignee: Howard S. Leight & Associates, Inc., Marina Del Rey, Calif.

[21] Appl. No.: 36,118

[22] Filed: Apr. 9, 1987

[51] Int. Cl.⁴ ............................................. A61F 11/00
[52] U.S. Cl. .................................................. 128/864
[58] Field of Search .................. 128/151, 152; 264/42, 264/45.5, 46.6, 51

[56] References Cited

U.S. PATENT DOCUMENTS

| | | | |
|---|---|---|---|
| Re. 29,487 | 12/1977 | Gardner, Jr. ....................... | 128/152 |
| D. 253,723 | 12/1979 | Leight ................................ | 128/152 |
| D. 264,249 | 5/1982 | Leight ................................ | D24/67 |
| 3,816,233 | 6/1974 | Powers ............................... | 264/45.5 |
| 3,872,559 | 3/1975 | Leight ................................ | 128/152 |
| 4,094,315 | 7/1978 | Leight ................................ | 128/152 |
| 4,119,583 | 10/1978 | Filip et al. .......................... | 264/46.6 |
| 4,131,662 | 12/1978 | Cekoric et al. ..................... | 264/51 |
| 4,164,526 | 8/1979 | Clay et al. .......................... | 264/45.5 |
| 4,434,794 | 3/1984 | Leight ................................ | 128/152 |
| 4,498,469 | 2/1985 | Csiki .................................. | 128/151 |
| 4,676,937 | 7/1987 | Brown et al. ...................... | 264/42 |

Primary Examiner—Robert A. Hafer
Assistant Examiner—Michael Brown
Attorney, Agent, or Firm—Freilich, Hornbaker, Rosen & Fernandez

[57] ABSTRACT

An earplug of the slow recovery type is described, which has open cells for expelling gas to the outside during compression, but which resists the entry of water through the outside and the soiling of the outside by dirt. The earplug includes a body formed of pressure-molded slow recovery resilient foam material forming multiple gas-filled shells. The plug body has a surface region forming a skin wherein the average cell cross-sectional area is less than half that of cells at the center of the body, and is less than one-tenth millimeter, the surface region being primarily continuous.

6 Claims, 1 Drawing Sheet

SLOW RECOVERY EARPLUG WITH LARGELY IMPENETRABLE SURFACE

BACKGROUND OF THE INVENTION

Slow recovery earplugs, such as the type described in U.S. Pat. No. Re. 29,487 have gained wide acceptance. Such earplugs can be rolled in the fingers to a small diameter, inserted into the ear, and allowed to expand over a period of between a few seconds to a few minutes to completely fill the end of the user's ear canal. Such earplugs have been previously formed by punching cylinders out of a thick sheet of slow recovery material, which is generally an open cell foam that allows air to escape when squeezing the earplug before insertion. Such earplugs easily pick up water or other fluids which hamper their use. Also, the multiple cut cells at the surface tend to pick up dirt, especially when a worker with dirty hands rolls the earplug between his fingers to compress it prior to insertion. A slow recovery earplug which resisted soiling and the pickup of water at its surface would be more sanitary and have a longer lifetime of use.

SUMMARY OF THE INVENTION

In accordance with one embodiment of the present invention, a slow recovery earplug is provided, which resists soiling especially during squeezing of the earplug to fit into the ear. The earplug includes a main body formed of pressure-molded slow recovery resilient foam plastic material that forms multiple gas-filled shells. The average cell diameter within the body decreases at locations progressively closer to the outside surface of the earplug, to provide a somewhat smooth surface which is devoid of large cells that could pick up dirt. The surface region forms a smooth skin that is largely imperious to solid and liquid contaminants. The same construction is useful in an earmuff.

The novel features of the invention are set forth with particularity in the appended claims. The invention will be best understood from the following description when read in conjunction with the accompanying drawings.

DESCRIPTION OF THE PREFERRED EMBODIMENT

Figure 1:
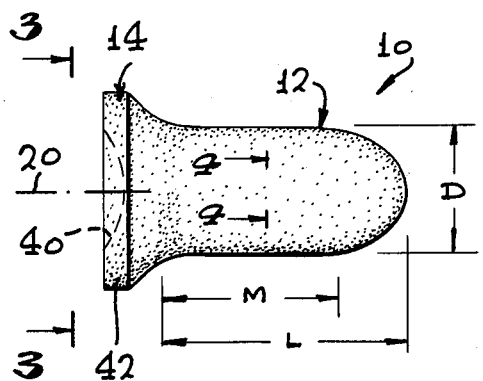
FIG. 1 is a side elevation view of an earplug constructed in accordance with the present invention, shown in its fully expanded condition.
Figure 2:
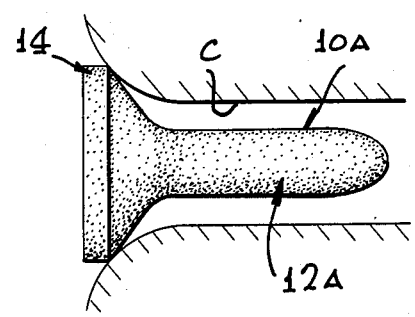
FIG. 2 is a view similar to that of FIG. 1, but showing the earplug in its fully compressed condition.
Figure 3:
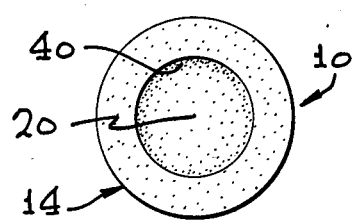
FIG. 3 is a view taken on the line 3—3 of FIG. 1.

FIG. 1 illustrates a slow recovery earplug 10 which includes a largely bullet-shaped main body portion 12 and a flared rear end 14. As indicated in FIG. 2, the main body portion is designed to be compressed to the configuration shown at 12A (FIG. 2) so it can be inserted into the ear canal C of a person. During a period of about one minute, the earplug expands to near its uncompressed configuration, and presses against the walls of the ear canal to block noise. As the main body portion of a slow recovery earplug is rolled in the fingers to compress it, liquid and solid foreign materials which may lie on the worker's fingers could be picked up by the earplug. The earplug is formed generally of an open cell material to enable the escape of air while the body portion is being compressed. In prior slow recovery earplugs, which were punched out of thick sheets of slow recovery material, large open cells were present at the surface of the earplug. Such large open cells easily absorb foreign material, so that the earplug could quickly become soiled, and could become damaged if it came in contact with water or other liquids.

The present earplug 10 is pressure molded from a slow recovery urethane foam material. This is accomplished by mixing the foam materials, placing them in a mold having a cavity of the shape shown in FIG. 1, and closing the mold, with a very small opening for escape of air such as a slit of about 0.2 millimeters width. The amount of foamable material is sufficient to fill a cavity of a volume greater than that of the finished earplug, so the material expands to the full size of the cavity and then presses with considerable pressure against the walls of the cavity. Sufficient foamable material is present that the pressure of the expanding foam against the mold walls is at least 0.5 psi; applicant uses about 2 psi for the examples of earplugs described herein. For lower pressures, such as those approaching zero pressure (the top of the mold is open) the cells near the skin are large, and can more easily pick up moisture and dirt.

The appearance of the surface is not as smooth as for the pressure-molded earplug. Applicant finds that the size of the gas-filled cells within the pressure-molded earplug is greatest at the center of the earplug, and decreases at locations progressively closer to the surface of the earplug. Furthermore, the earplug forms a skin at the surface where the pores are very small, and with most of the skin area being substantially closed. As a result, there are few openings at the outer surface for picking up and retaining liquid and soiling material. Thus, such foreign material tends not to be absorbed into the earplug, so that the earplug's surface tends to remain clean and the lifetime of use of the earplug is longer than those of the prior art described above.

Figure 4:
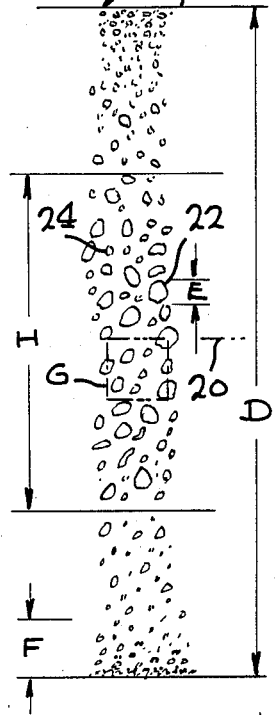
FIG. 4 is an enlarged view of a section of the earplug of FIG. 1, taken on the line 4—4 of FIG. 1.
Figure 5:
FIG. 5 is an enlarged view of a portion of the surface of the earplug of FIG. 1.
Figure 6:
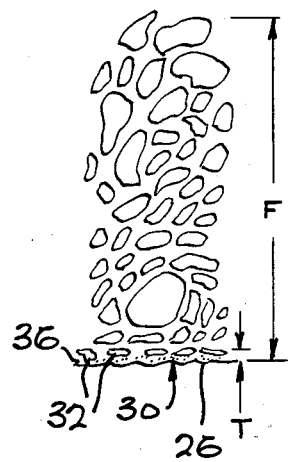
FIG. 6 is an enlarged view of a portion of the earplug section of FIG. 4, near the surface of the earplug.

FIG. 4 illustrates a portion of a cross section of the earplug main body portion 12 of FIG. 1. The earplug main body portion 12 has a substantially cylindrical outer surface (if of polygon cross-section there are many faces so it is of substantially circular cross-section, and any taper angle is small) having a diameter D of about 11 mm (millimeters) along most of its length and is formed of multiple gas-filled cells that each has a width of a plurality of thousandths of an inch. Near the center or axis 20, the earplug includes numerous large cells 22 of a diameter E of at least 0.2 mm. A plurality of such large cells lie in each square millimeter G of a majority of the cross-sectional area of the earplug at the middle H (which is one-half D). Small cells 24 of an average diameter less than 0.2 mm lie interspersed with the large cells. The cross-sectional area occupied by large cells of over 0.2 mm diameter decreases at locations progressively closer to the surface 26 of the earplug. Within a distance F of one millimeter from the earplug surface, there are twice as many cells, which are small, in each square millimeter of cross-sectional area than at the middle region of height H. The average cross-sectional area of the cells within one-half millimeter of the surface is less than half the average cross-sectional area of cells within the central 5 mm of the main body portion. The decrease in cell size near the surface results in resistance to the soiling of the earplug. It is also found that the pressure-molded earplug develops a skin 30 (FIG. 6) of a thickness T of about 0.05 mm, with most cells 32 nearest the skin being of about 0.05 to 0.1 mm diameter and spaced about 0.05 mm from the outside or surface 26 to form the skin 30 between those cells 32 and the surface 26. As shown in FIG. 5 which shows a view of the skin from the outside, the skin includes numerous shallow recesses 34, and with only a limited number of holes through which air can escape and through which liquids and dirt can be absorbed into the earplug.

The skin also includes talcum powder 36 embedded therein, which is produced by coating the mold surface with talcum powder before pouring in the foam material. Applicant finds that the outside of the earplug has a relatively low friction against the skin, which facilitates its removal from the ear, and is substantially smooth and rejects the instrusion of dirt therein.

The flanged or flared rear end 14 of the earplug limits the depth of insertion of the earplug into the ear, and also provides a region to be grasped to remove the earplug from the ear canal. Because of the flange, users tend to roll only the bullet-shaped or largely cylindrical body 12, while leaving the flanged end 14 at its full size. This reduces the possibility of deep insertion of the compressed earplug into the ear, and it reduces the difficulty of removing the earplug. The main body portion of length L is of substantially uniform width ($\pm 10\%$ of the width D at the middle) along a distance M which is most of the length of the main portion. To facilitate grasping of the flanged rear end, applicant includes a recess 40 in the rear of the earplug along the axis 20 to provide a thinner outer region 42 to facilitate grasping of this region to pull out the earplug. The recess 40 also avoids bulging of the rear end when the main body portion is compressed, such bulging resisting full insertion of the main body portion in the ear canal.

Figure 8:
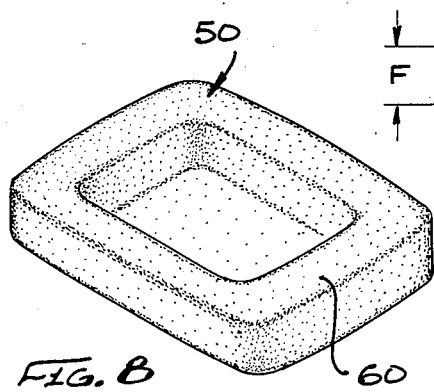
FIG. 8 is a perspective view of the earmuff portion of FIG. 7.
Figure 7:
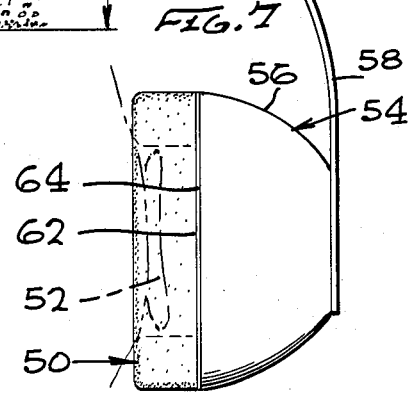
FIG. 7 is a partial side view of an earmuff constructed in accordance with another embodiment of the invention.

FIGS. 7 and 8 illustrate another ear sound-blocking member in the form of an earmuff portion or earmuff 50, which is formed of the same pressure-molded slow recovery resilient foam plastic material as the earplug described above. The earmuff 50 comprises at least a portion extending in a closed loop of a width and length that are each of a plurality of centimeters, and which can extend around the ear 52 of the wearer. The earmuff 50 is designed to be held on a band device 54 which includes a mount 56 held by a band 58 that extends halfway around a person's head and which resiliently holds a pair of earmuffs against the regions of a person's head around his ears. The slow recovery material slowly adjusts well to the contours of the particular wearer to effectively block sound. The use of pressure-molded slow recovery material results the surface 60 of the earmuff resisting the pickup of moisture and dirt, which could result in a less sanitary earplug and one with a shorter lifetime of use.

The earmuff 50, like the earplug described above, is of urethane foam that is molded in a closed mold, which has only a small thin opening for the escape of air from the mold while substantially preventing the escape of foaming plastic. The urethane foam is kept in the mold at a pressure of at least 0.5 psi, and preferably about 2 psi. The particular earmuff 50 is designed to be mounted by adhesive tape 62 on a surface 64 of the mount.

Thus, the invention provides an ear sound-blocking member which is an earplug or earmuff of slow recovery material, which avoids soiling or absorption of liquid therein. The member includes a pressure-molded slow recovery resilient foam plastic material which forms multiple gas-filled cells, and which has been formed in a closed mold at a pressure of at least 0.5 psi. The member includes a surface region within one millimeter of the surface of the body, where the average cell size is less than half the size of cells at the center of the member. The member also forms a skin which is primarily closed in that there are compressed small cells spaced from the outside to form a generally solid (generally unperforated by visible cells) skin between such elongated small shells and the outside of the member. The earplug has a flared rear end that tends not to be compressed by persons, and which therefore helps avoid too deep insertion into the ear canal.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:
1. An earplug comprising:
an earplug body having a main body portion forming a largely cylindrical outer surface and constructed to enable its reception in the ear and having outer walls adapted to directly contact the surface of the ear canal, said body formed of pressure-molded slow recovery resilient foam plastic material forming multiple gas-filled open cells which permits rolling of the main body portion to a temporarily reduced diameter, with the average cross-sectional area of cells being less near substantially the entire largely cylindrical surface of the main body portion than at the middle of the cross-section of the main body portion, said outer walls being porous to allow the escape of air.

2. The earplug described in claim 1 wherein:
said plastic material is a urethane foam which has been molded under a pressure of at least about 0.5 psi in a closed mold.

3. The earplug described in claim 1 wherein:
said largely cylindrical main body portion has a predetermined length and has a diameter of about 11 millimeters along most of its length, and said body is formed of urethane foam.

4. The earplug described in claim 1 wherein:
said body has a flared rear end of greater diameter than said main body portion, said main body portion having a predetermined length and being of substantially uniform width along most of its length, whereby to encourage rolling of only the main body portion but not the rear end.

5. An earplug comprising:
an earplug body having a largely bullet-shaped main body portion having an outer surface of a substantially circular cross-section of a width of about 11 millimeters for fitting into a human ear canal, and having a flared rearward portion of greater diameter than said main body portion, said body constructed of a pressure-molded slow recovery urethane foam forming multiple cells;

said main body portion having numerous gas-filled visible open cells that are each of a diameter of a plurality of thousandths inches, the average cross-sectional area of said visible open cells in a region within one-half millimeter of said substantially circular outer surface being less than half the average cell cross-sectional area of said visible cells within the central 5 millimeters of the width of said main body portion.

6. The earplug described in claim 5 wherein:

said visible cells include a plurality of large cells of diameters of a plurality of tenths of millimeters, in each square millimeter of said central 5 millimeters of width; and said main body portion has a pressure-molded skin of a thickness on the order of one-twentieth millimeter, which is substantially continuous.

* * * * *